United States Patent [19]

Bonds

[11] Patent Number: Plant 7,497

[45] Date of Patent: Apr. 16, 1991

[54] ALMOND TREE, CRUZ

[75] Inventor: Irwin H. Bonds, Hilmar, Calif.

[73] Assignee: Ruben A. Cruz, Modesto, Calif.

[21] Appl. No.: 422,412

[22] Filed: Oct. 16, 1989

[51] Int. Cl.[5] ..... A01H 5/00

[52] U.S. Cl. ..... Plt./30

[58] Field of Search ..... Plt./30

*Primary Examiner*—James R. Feyrer

*Attorney, Agent, or Firm*—Worrel & Worrel

[57] ABSTRACT

A new and distinct variety of almond tree denominated varietally as "Cruz" and which is characterized as to novelty by a date of maturity for commercial harvesting and shipment of approximately September 5 under the ecological conditions prevailing at Hickman, Calif., in the Central part of the San Joaquin Valley of Central California.

1 Drawing Sheet

BACKGROUND OF THE NEW VARIETY

The present invention relates to a new and distinct variety of almond tree, hereinafter denominated varietally as "Cruz", and which is somewhat similar in its overall physical characteristics to the Nonpareil almond tree (unpatented), but from which it is distinguishable therefrom and characterized principally as to novelty by producing a crop which is ripe for harvesting and shipment approximately seven to ten days after the Nonpareil variety of almond tree, that is, September 5, under the ecological conditions prevailing in the San Joaquin Valley of Central California.

In a continuing effort to upgrade the quality of his employer's agricultural products, the inventor is constantly on the alert to locate any new varieties of trees that may appear from time to time as chance seedlings or mutations, in the commercial orchards, or other agricultural areas under his supervision and control. In connection with these labors, the applicant, in 1970, discovered a chance seedling of unknown parentage, growing in the cultivated area of the public right of way at the corner of Livingston and Cressey Roads, north of Cressey Way, in Cressey, Calif.

ORIGIN AND ASEXUAL REPRODUCTION OF THE NEW VARIETY

The present variety of almond tree was a chance seedling of unknown parentage which was discovered within the cultivated area of the public right of way on the Livingston-Cressey Road, north of Cressey Way, in Cressey, Calif. The subject variety was observed at that time to have desirable characteristics and it was thereafter asexually reproduced by the inventor by removing buds, in 1978, from the original chance seedling and by budding them into test seedlings which were then growing on the Dave Wilson Nursery growing grounds located on Lake Road, in Hickman, Calif. These budded test seedlings have been continually observed and evaluated by the inventor and it has subsequently been determined that the progeny produced by these test seedlings possess the same distinctive characteristics as the original chance seedling.

SUMMARY OF THE NEW VARIETY

The almond tree of the present invention is noteworthy in ripening approximately September 5 under the ecological conditions prevailing in Hickman, Calif., the subject variety maturing for harvesting and shipment approximately seven to ten days after the Nonpareil Almond Tree (unpatented) at the same geographical location.

BRIEF DESCRIPTION OF THE DRAWINGS

The accompanying drawing is an illustration by photographic reproduction of a portion of a branch of an almond tree of the new variety showing a mature crop arranged in clusters along the branch. Further, the drawing also illustrates mature whole nuts, both with and without the shells removed, which are representative of the crop borne by the new variety of almond tree, denominated varietally as "Cruz".

DETAILED DESCRIPTION

Referring more specifically to the botanical details of this new and distinct variety of almond tree, the following has been observed under the ecological conditions prevailing at the orchard of the inventor's employer which is located in Hickman, Calif. All major color code designations are by reference to the Inter-Society Color Council, National Bureau of Standards. Common color names are also employed occasionally.

TREE

Size:

*Generally.*—Average as compared with other common almond tree varieties which can grow in this general geographical location.

Density: Upright and open, depending upon pruning practices.

Vigor: Average.

Regularity of bearing: Regular.

Rootstock compatability: The subject variety "Cruz" is compatible with Marianna 2624 rootstock. This compatability is in stark contrast to the Nonpareil variety of almond tree which cannot be grown on the aforementioned root stock.

Trunk:

*Size.*—Medium.

*Surface texture.*—Normal as compared with other common almond tree varieties.

Branches:

*Size.*—Average.

*Surface texture.*—Average as compared with other common almond tree varieties.

Lenticels:

*Numbers.*—Numerous.
*Size.*—Average.
Branching habit: Average, depending upon pruning practices.
Color:
*New Growth.*—Green, (120 m. Y. G). The exposed surfaces of some new growth may be tinged red (13. deep Red - 16. d. Red).
*One year or older wood.*—Brown, (58. m. Br).

LEAVES

Foliage quantity:
*Generally.*—Average as compared with other almond tree varieties which will grow in approximately the same geographical area.
Size:
*Generally.*—Average.
*Average length.*—Approximately 3½", (88.9 mm.).
*Average width.*—Approximately 1¼", (31.75 mm.).
Shape:
*Generally.*—Acuminate.
Tip:
*Shape.*—Acutely pointed.
Base:
*Shape.*—Oblique.
Thickness:
*Generally.*—Average as compared with other common almond tree varieties which will grow in approximately the same geographical area.
Marginal form: Coarsely serrate.
Petiole:
*Length.*—Average.
*Thickness.*—Medium.
Glands:
*Generally.*—No glands are evident.
Color:
*Upwardly disposed surface.*—Green, (125. m. Ol G).
*Downwardly disposed surface.*—Yellow Green, (120 m. y G).
Bloom:
*Amount.*—Heavy as compared with other common almond tree varieties which are grown in the same geographical area.
Bloom color: Pink. The color is not particularly distinctive of the subject variety.
Date of bloom: Early as compared with other common almond tree varieties. The subject variety "Cruz" blooms approximately three days before the Nonpareil Almond Tree at Hickman, Calif. Further, the almond tree "Cruz" blooms over a longer period of time thereby facilitating the pollenization of other almond trees growing in the same geographical vicinity.

FRUIT

Productivity: Heavy as compared with other common almond tree varieties. Moreover, the variety "Cruz" yields a more consistent crop from year to year.
Distribution of nuts on the tree: Well distributed throughout.
Ripe for commercial harvesting and shipment: Approximately 7 to 10 days after the Nonpareil variety of almond tree, that is, approximately September 5 near Hickman, Calif.
Harvesting:
*Generally.*—The subject variety "Cruz" hangs well on the tree during harvesting and is considered easy to harvest and easy to hull as compared with other common almond tree varieties.
Hull:
*Outside surface texture.*—Smooth.
Pits:
*Generally.*—Pitted.
Form:
*Generally.*—Considered regular.
Hull thickness: Thin, as compared with other almond tree varieties.
Flesh:
Texture.—Tough.
Suture:
*Shape.*—Flat and depressed.
Hull color: Light green and having a silvery sheen, (120. m. y G).
*Blush.*—Tan, (58. m. Br).
Dehiscence: The subject variety opens freely.
Splitting:
*Generally.*—Splitting occurs along the suture.

NUT

Size:
*Generally.*—Average as compared with other common almond tree varieties.
*Average length.*—Approximately 1⅛", (28.575 mm.).
*Average width.*—Approximately ¾", (19.050 mm.).
*Average thickness.*—Approximately ½", (12.7 mm.).
Form:
*Generally.*—Considered ovate.
Thickness: Considered plump.
Shell:
*Surface texture.*—Soft, thin, and ragged. Outer shell — Surface texture — Crumbling. Inner shell — Surface texture — Soft and considered well sealed. This appears to be in contrast to the Nonpareil variety which is not considered to be well sealed.
Color: Variable, dark brown, (76. l. y Br–77. m. y Br).
Pits:
*Size.*—Small.
*Numbers.*—Numerous.
*Depth.*—Shallow, and irregularly shaped.
Base:
*Shape.*—Square.
Stem scar:
*Size.*—Large and obtusely positioned.
Apex:
*Shape.*—Blunt.
Wing:
*Shape.*—Thin and narrow. Further the wing is tapered toward the apex.
Inner surface:
*Color.*—Darkly colored. The color is not distinctive, however.
Ventral streak:
*Color.*—Dark, narrow, and short. The ventral streak has an acute point.
Percent of kernel to nut: Approximately 60%.

KERNEL

Size:
*Generally.*—Considered average as compared with other common almond tree varieties.
*Average length.*—Approximately ⅞", (22.225 mm.).
*Average width.*—Approximately ⅝", (15.875 mm.).
*Average thickness.*—Approximately ⅜", (9.525 mm.).

Form:

*Generally.*—Considered rounded.

Thickness:

*Generally.*—Average as compared with other almond tree varieties.

Base:

*Shape.*—Square.

Stem scar:

*Shape.*—Small.

Apex:

*Shape.*—Sharp.

Surface texture: Wrinkled.

Pellicle:

*Thickness.*—Thin.

Pubescence:

*Generally.*—Medium.

Color: Light brown, (57 I. Br).

Numbers of doubles produced: Few.

Flavor: Average as compared with other almond tree varieties.

Quality: Good.

Susceptibility to common diseases: The subject variety "Cruz" displays an increased resistance to brown rot disease, as compared with the Nonpareil variety of almond tree.

Although the new variety of almond tree possesses the described characteristics when grown under the ecological conditions prevailing in Hickman, Calif., in the Central part of the San Joaquin Valley, it is to be understood that variations of the usual magnitude and characteristics incident to changes in growing conditions, fertilization, pruning and pest control are to be expected.

Having thus described and illustrated my new variety of almond tree, what is new and desired to be secured by Letters Patent is:

1. A new and distinct variety of almond tree substantially as illustrated and described and which is somewhat similar to the Nonpareil almond tree (believed unpatented) which matures at approximately the same time of the season, but which is distinguished therefrom and characterized principally as to novelty, by producing a crop which is ripe for commercial harvesting and shipment approximately seven to ten days after the Nonpareil variety of almond tree and which further has a longer blooming period than the Nonpareil variety of almond tree, the new variety of almond tree "Cruz" facilitating the pollenization of other almond trees growing in the immediate geographical vicinity thereof.

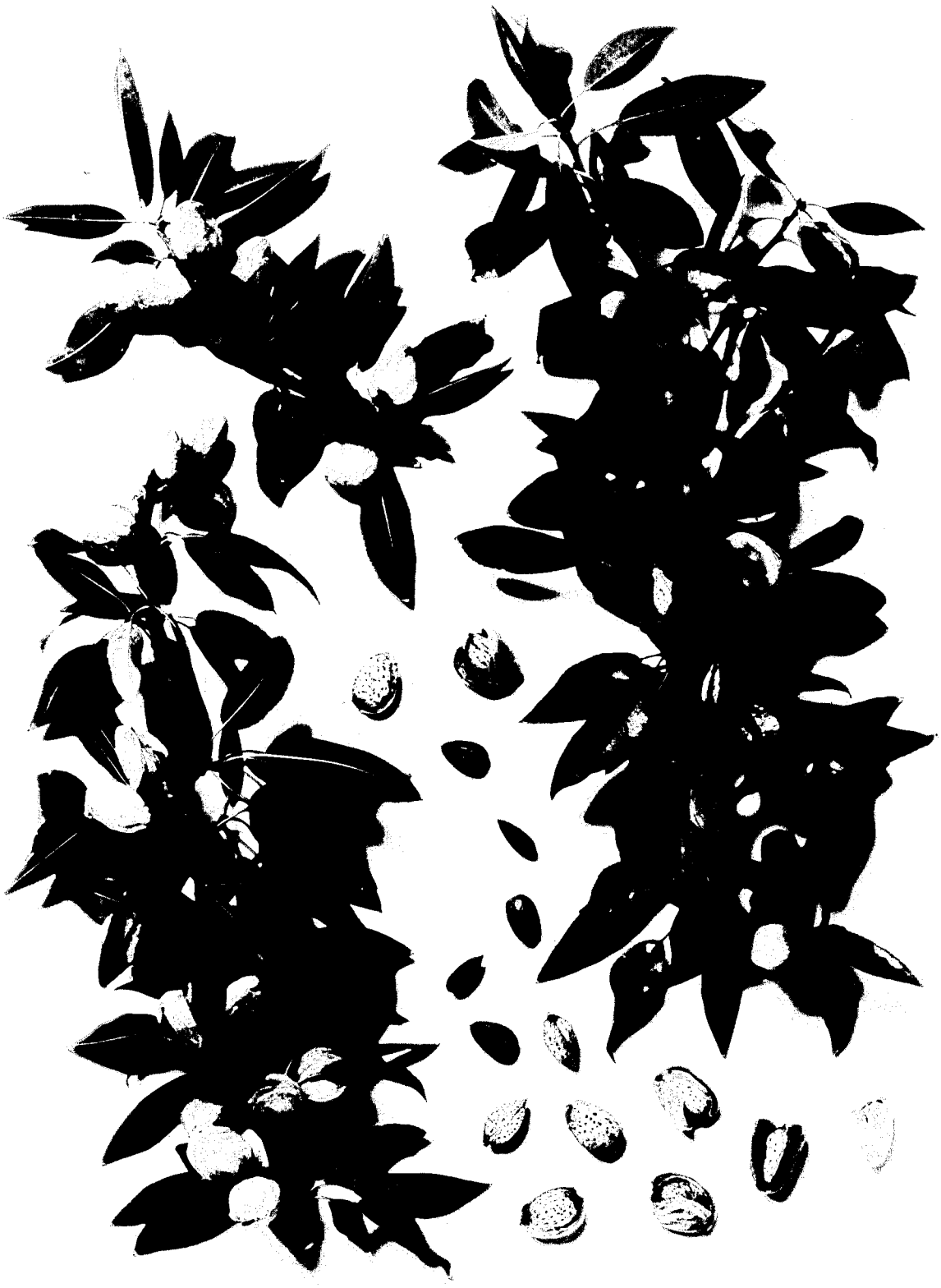

* * * * *